(12) United States Patent
Lind

(10) Patent No.: US 6,188,077 B1
(45) Date of Patent: Feb. 13, 2001

(54) METHOD AND MEASURING MACHINE FOR ANALYZING A PAPER WEB

(75) Inventor: Bengt Lind, deceased, late of Rättvik (SE), by Ella-Britt Lind, executrix

(73) Assignee: Stora Kopparbegs Bergslags AB, Falun (SE)

( * ) Notice: Under 35 U.S.C. 154(b), the term of this patent shall be extended for 0 days.

(21) Appl. No.: 09/284,511

(22) PCT Filed: Oct. 13, 1997

(86) PCT No.: PCT/SE97/01708

§ 371 Date: May 12, 1999

§ 102(e) Date: May 12, 1999

(87) PCT Pub. No.: WO98/16816

PCT Pub. Date: Apr. 23, 1998

(30) Foreign Application Priority Data

Oct. 15, 1996 (SE) .................................................. 9603765

(51) Int. Cl.[7] .................................................. G01N 21/86
(52) U.S. Cl. .................... 250/559.01; 356/429; 427/9; 118/419; 162/263
(58) Field of Search ........................ 250/559.01, 559.24, 250/559.36; 356/429; 162/198, 263, 265; 118/419, 665, 688; 427/9, 10, 434, 2

(56) References Cited

U.S. PATENT DOCUMENTS

| | | | |
|---|---|---|---|
| 3,619,359 | * 11/1971 | Keyes | 162/252 |
| 3,622,448 | * 11/1971 | Adams et al. | 162/198 |
| 4,770,538 | * 9/1988 | Orkosalo | 356/429 |
| 4,789,820 | * 12/1988 | Parrent, Jr. et al. | 324/58.5 R |
| 4,957,770 | * 9/1990 | Howarth | 427/9 |
| 5,019,710 | * 5/1991 | Wennerberg et al. | 250/341 |
| 5,022,966 | * 6/1991 | Hu | 162/198 |
| 5,092,678 | * 3/1992 | Chase et al. | 356/429 |
| 5,243,407 | * 9/1993 | King et al. | 356/429 |
| 5,399,859 | * 3/1995 | Gray et al. | 250/308 |
| 5,455,422 | * 10/1995 | Anderson et al. | 250/341.1 |
| 6,074,483 | * 6/2000 | Belotserkovsky et al. | 118/665 |
| 6,099,690 | * 8/2000 | Hu et al. | 162/198 |

FOREIGN PATENT DOCUMENTS

| | | |
|---|---|---|
| 1 196 512 | 11/1985 | (CA) . |
| 3336659 | 4/1984 | (DE) . |
| 0240610 | 10/1987 | (EP) . |
| 0267712 | 5/1988 | (EP) . |
| 0380412 | 8/1990 | (EP) . |
| 0390623 | 10/1990 | (EP) . |
| 0628794 | 12/1994 | (EP) . |

* cited by examiner

Primary Examiner—Stephone B. Allen
(74) Attorney, Agent, or Firm—Nixon & Vanderhye P.C.

(57) ABSTRACT

A method and a measuring machine for analyzing at least one property of a paper web (7). According to the invention a jumbo roll (5) from a paper machine is placed in a measuring machine and its paper web (7) is conveyed from an unreeling section (1), through a measuring section (3) to a reeling section (2). A measuring sequence is performed which comprises stepwise feeding of the paper web and measuring the property in the measuring section, when the paper web is stationary, within a web-width measuring area which in the machine direction corresponds to said step length, by scanning traversing a measuring sensor. The values recorded are transmitted to a computer unit for processing and conversion to a visual form.

12 Claims, 3 Drawing Sheets

METHOD AND MEASURING MACHINE FOR ANALYZING A PAPER WEB

The present invention relates to a method of analyzing at least one property of a paper web manufactured in a defined paper machine from which jumbo rolls are supplied.

The invention also relates to a measuring machine for analyzing at least one property of a paper web manufactured in a defined paper machine from which jumbo rolls are supplied.

The manufacture of paper comprises a large number of part processes, each of which affects inter alia the quality of the product. The paper shall have certain properties in accordance with the customer's wishes. Furthermore, the properties shall be constant, i.e. shall lie within defined limits, in order to achieve uniform quality. Although the properties can be specified at the time of ordering, the manufacturer by experience usually believes he knows what the product should be like in order to comply with the wishes of the customer, and the manufacturer then determines internal specifications for the part processes and their parameters in an endeavour to follow these.

However, the information currently available concerning quality properties of the paper supplied by a paper machine is extremely limited. The information is based on the measurement of very small quantities of the paper in a reel for delivery to a customer and it must be assumed that the properties measured in these small, restricted amounts of paper are representative for all the paper in the reel. This circumstance constitutes an essential obstacle to the technical development of paper and paper products.

The measuring system of a paper machine measures less than 0.5% of the total surface of the paper web which is to make up a jumbo roll. Furthermore, the measurement is performed diagonally over the paper web and detailed information disappears since the results are converted to mean values. However, such detailed information is of great significance to the properties of the final product. The properties of the paper are also determined in the laboratory on cut samples representing less than 0.1 per mille of the total area of the paper web which is to make up a jumbo roll.

The object of the present invention is to eliminate the above-mentioned problems.

The method according to the invention is characterized in that a jumbo roll from said paper machine is placed in a measuring machine, that the paper web is conveyed from an unreeling section for the jumbo roll, through a measuring section to a reeling section for winding the paper web to form a new reel, that a first measuring sequence is performed which comprises feeding the paper web in a plurality of steps having the same predetermined length, and measuring said property in the measuring section, when the paper web is stationary, within a web-width measuring area which in the machine direction corresponds, or substantially corresponds to said step length, by scanning traversing a measuring sensor, in order to measure said property from one edge of the paper web to the other within said measuring area, and that the measured values recorded by the measuring sensor are transmitted to a computer unit for processing and conversion of the measured values to a visual form which indicates variations of the property within an area of the paper web defined by said steps. According to a preferred embodiment of the invention the measured values are converted to graphic form, and most preferably are presented by cartogram.

The measuring machine according to the invention is characterized in that it comprises an unreeling section to support and rotatably journalling a jumbo roll from said paper machine, a reeling section for winding the paper web of the jumbo roll to form a new reel and a measuring section situated between them through which the paper web passes, that the measuring section comprises traversing scanners having a measuring sensor for measuring said property, that the reeling section includes drive means for stepwise movement of the paper web through the measuring section, and that the measuring section includes a computer unit for storing the measured values recorded by the measuring sensor and processing these values for visual presentation of variations of the property.

The use of the method and the measuring machine according to the invention entails an advanced total analysis of the paper web which enables a practically complete and two-dimensional representation of the properties of the paper web in a jumbo roll to be obtained with a resolution of 1 cm$^2$. The information obtained through the advanced total analysis of the paper web is useful in many contexts.

The information can be used as follows, for instance:

A. For in-house process development. It provides a clearer representation of the function mode of various process apparatus and their interaction than has been possible previously and in this way form the basis for making improvements.

B. For in-house product development. It facilitates opportunities for developing a paper with the properties desired by the customer and creates new possibilities of more accurately and distinctly mapping out and documenting paper properties.

C. For customer process development. It offers customers an excellent basis on which to determine the setting of their conversion equipment and opportunity to improve this.

D. For customer product development. The properties of the paper supplied greatly influence the quality of the customer's final product. The information enables the customer to make better assessments than before, and more clearly inform the supplier what paper properties are required in order to achieve a satisfactory final product.

The invention involves that a comprehensive, fine-scale measurement to be performed of a web-width area until the variation pattern of the properties appear. This comprehensive, fine-scale measurement means that every small surface unit within said web-width area is measured. One such small surface unit for said first measuring sequence, using present-day measuring equipment, is 1 cm$^2$.

The values measured are processed directly by a computer unit which presents the result in the form of a topographical map, i.e. a cartogram, preferably coloured, in which each colour represents a certain value of the properties. The cartogram may reveal an undesired irregularity in a measured property which may be caused by errors in the operating parameters set and/or in construction elements of the paper machine from which the paper web under analysis comes. A cartogram over a grammage analysis may, for instance, reveal regularly occurring diagonal larger or smaller areas with increased grammage in comparison with the adjacent areas, which may originate from preparation of the pulp fed to the paper machine. A grammage cartogram showing recurrent round patches in a certain pattern may be caused by deficiencies in the wire section, e.g. the dewatering system. Keeping the pulp in a pulp vessel at the wrong level may result in a grammage cartogram with large patches. A grammage cartogram in which grammage variations appear in a striped pattern may be caused by a pulp pump which is not centred so that small pulses occur in the pulp as it is pumped out of the headbox. Advantageously, the effect of rebuilding a paper machine can easily be verified by comparing cartograms obtained before and after the rebuilding.

The properties that may be of interest for analysis and measurement in accordance with the invention are grammage, thickness, moisture content, ash content, strength and optical properties of the paper web.

The invention will be described in more detail with reference to the accompanying drawings.

Figure 1:
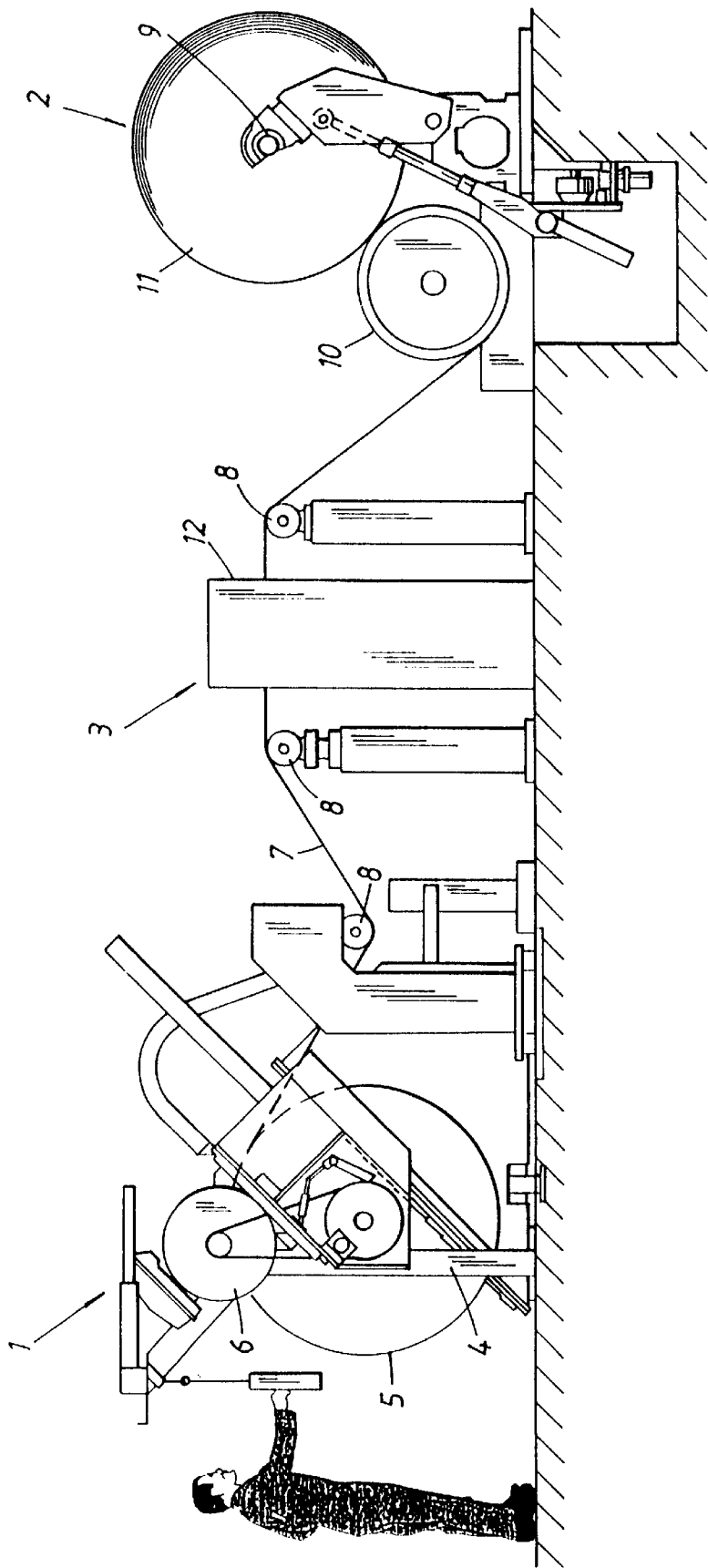
FIG. 1 is a side view of a measuring machine according to the invention.

FIG. 1 shows schematically a measuring machine according to the invention which can in principle be likened to an extended and supplemented rewinder. The measuring machine has an unreeling section 1, a reeling section 2 and a measuring section 3 situated therebetween. The unreeling section 1 comprises a stand 4 to support and journal a jumbo roll 5, and a braking device 6 to control the rotary movement of the jumbo roll 5. The paper web 7 of the jumbo roll 5 is conveyed over a plurality of guide rolls 8 up to the reeling section 2 which is designed as a drum reel-up comprising a reeling drum 9 and a surface winding drum 10 around which the paper web 7 runs to form a paper reel 11 on the reeling drum 9. The paper reel 11 rests on the surface winding drum 10 and is driven by this by means of friction. The surface winding drum 10 is driven by a special drive means (not shown) enabling the paper web 7 to be moved forward stepwise with adjustable step lengths and to be fed at different, adjustable, uniform speeds. In the embodiment shown the measuring section 3 has a measuring frame 12. One or more additional measuring frames may be arranged if so desired. The measuring frame 12 is arranged transverse to the paper web 7 and is provided with an opening through which the full machine width of the paper web 7 passes. The measuring frame 12 includes a plurality of measuring sensors for measuring different properties of the paper web 7. The measuring sensors are movable along the measuring frame 12, i.e. perpendicular to the machine direction.

The jumbo roll 5 to be tested thus constitutes a paper reel which has been wound with full machine width in the reel-up of a paper machine. The jumbo roll may be one which is to be supplied to a customer or has been returned by a customer who makes a complaint about it.

Figure 2:
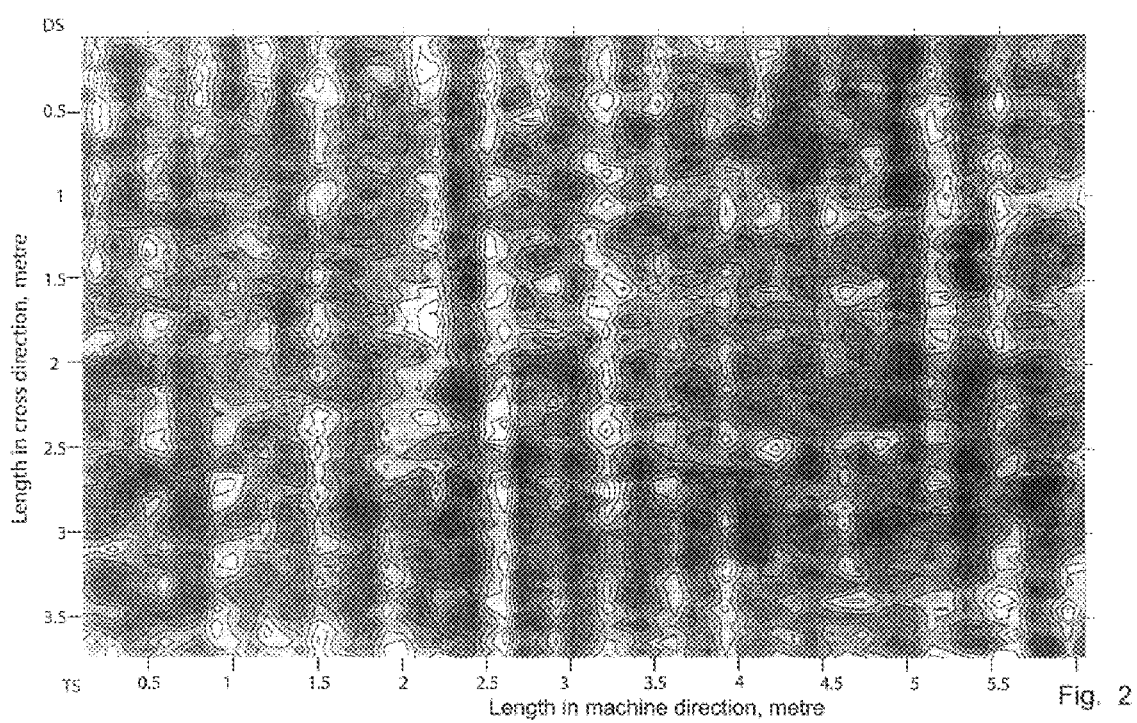
FIGS. 2 and 3 show two grammage cartograms produced in accordance with the invention, for paper webs manufactured before and after an alteration made to a defined paper machine.
Figure 3:
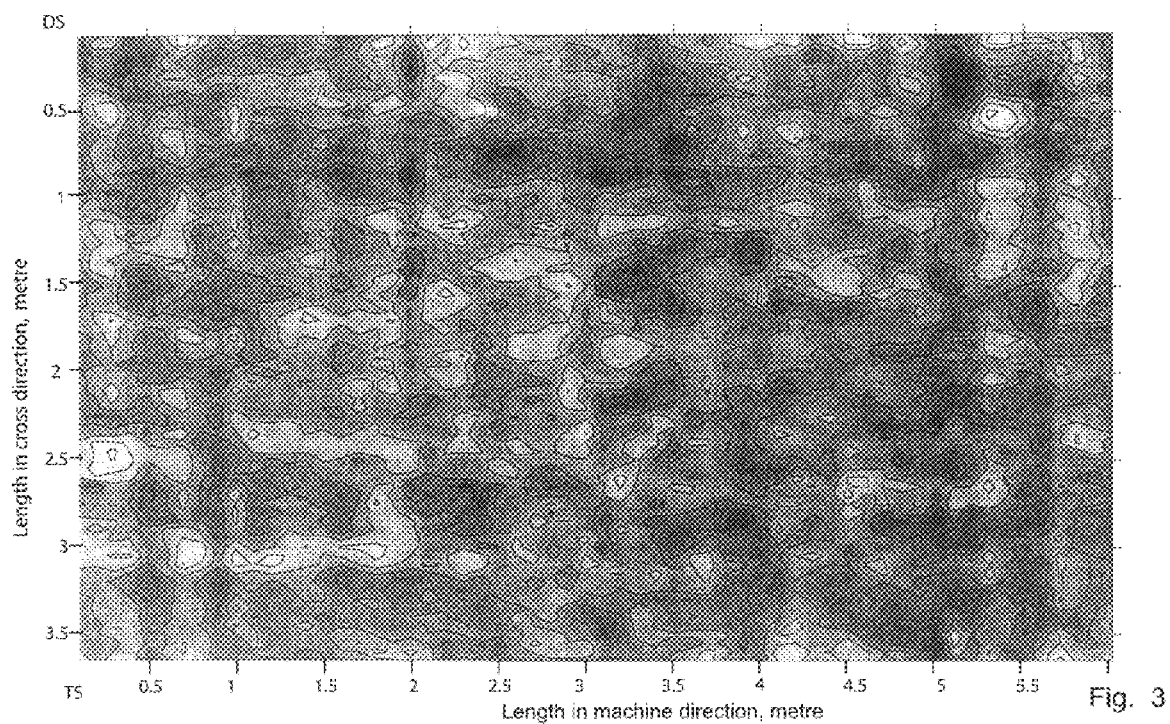

The following is a description of measuring the grammage of the paper web 7, the measuring frame 12 being equipped with a measuring sensor in the form of a grammage meter which is moved to and fro across the paper web between the edges of the web. Measurements are taken in both directions after a step movement. The measurements are carried out in a first measuring sequence while the web is stationary, and the web is stepped forward a predetermined distance every time the grammage meter reaches an edge of the web. Each edge-to-edge measurement takes place within a narrow transverse area and the following narrow transverse area is immediately adjacent to the previous one with no space or substantially no space between them. The values measured are transmitted continuously to a computer unit for recording and processing. The measured values show variations in the grammage at different measuring points within the same transverse area and within different transverse areas. The measured values are inserted on a topographical map, different nuances indicating different grammages. Cartograms of this type are shown in FIGS. 2–4. This first measuring sequence is performed until the variation pattern in the grammage is known. 2–8 metres of the paper web is normally sufficient to provide such a variation pattern.

A second measuring sequence is then usually performed, during which the paper web is fed continuously forward at low speed, e.g. 1 metre/minute, while simultaneously the grammage meter is traversing. Desired information concerning variations in the grammage can be obtained when a length of e.g. 10 metres of the web has been fed forward at this speed. One or more additional measuring sequences may then follow with stepwise increased speeds. During the third measuring sequence, which may be the last one in the first measuring series, traversing measurements are performed at a web speed of 100 m/min. over a longer distance. The measuring sequences can then be repeated in further measuring series on one or two subsequent web sections in order to verify the first measuring results. Between two consecutive series of measuring sequences and before the first and after the last series of measuring sequences, it is suitable to carry out length measurements of the grammage with the aid of 3–4 grammage meters disposed in suitable CD positions (in cross direction). The web is then run at a suitable speed of over 100 m/min. so that maximum information concerning the grammage can be obtained within a reasonable period of time, e.g. 24 hours.

Using present-day measuring equipment for grammage a resolution of 1 $cm^2$ can be obtained, i.e. each surface unit measured and recorded is 1 $cm^2$, but measuring equipment of the future is expected to be able to manage even smaller resolutions. If even more fine-scale information is desired to supplement the fine-scale (resolution 1 $cm^2$) information obtained with the described measuring machine, one or more samples of varying size can be taken from the actual paper web and measured in the laboratory, using an x-y-scanner which measures with a resolution of 1 $mm^2$, and equipment for beta radiogram which measures with a resolution of 0.1 $mm^2$.

In a test a paper web was analyzed in accordance with said first measuring sequence, the web having been manufactured in a defined paper machine for obtaining base paper for a coated fine paper product. The grammage of the base paper was 70 $g/m^2$. The measured values were presented in a cartogram, shown in FIG. 2 in a grey tone scale but which in reality is coloured. Each line represents a border between two surfaces with a difference in grammage of 1 $g/m^2$. The darkest areas have the highest grammage, about, 74.5 $g/m^2$, whereas the lightest areas have the lowest grammage, about 67.5 $g/m^2$. As is clear from the grammage cartogram in FIG. 2, the variations in grammage appear as a striped pattern, that is with longitudinal variations (cyclic MD-variation). The fault was assumed to be caused by an uncentered pulp pump which was producing small pulses in the pulp as it was pumped out of the headbox in the paper machine. After rectification of the fault the paper web was analyzed again and the measured values were presented in a cartogram, as shown in FIG. 3 in a grey tone scale. It can be seen that the striped pattern no longer appears and that the grammage distribution has been improved.

With the expression "a paper web manufactured in a defined paper machine from which jumbo rolls are supplied" is meant substantially that the analyze is carried out of a paper web the origin of which being known at least with respect to the mill where the paper machine is installed and/or the supplier of the jumbo roll.

What is claimed is:

1. A method of analyzing at least one property of a paper web (7) manufactured in a defined paper machine from which jumbo rolls (5) are supplied, characterized in that a jumbo roll (5) from said paper machine is placed in a measuring machine, that the paper web (7) is conveyed from an unreeling section (1) for the jumbo roll (5), through a measuring section (3) to a reeling section (2) for winding the paper web (7) to form a new reel (11), that a first measuring sequence is performed which comprises feeding the paper web (7) in a plurality of steps having the same predetermined length and measuring said property in the measuring section (3), when the paper web (7) is stationary, within a web-width measuring area which in the machine direction corresponds, or substantially corresponds to said step length, by scanning traversing a measuring sensor, in order to measure said property from one edge of the paper web (7) to the other within said measuring area, and that the measured values recorded by the measuring sensor are transmitted to a computer unit for processing and conversion of the measured values to a visual form which indicates variations of the property within an area of the paper web (7) defined by said steps.

2. A method as claimed in claim 1, characterized in that said first measuring sequence is performed within a length of 2-8 metres of the paper web (7).

3. A method as claimed in claim 1, characterized in that at least the first measuring sequence is performed at at least one additional portion of the paper web (7).

4. A method as claimed of claim 1, characterized in that it is utilized for one or more of the properties grammage, thickness, moisture content, ash content, strength and optical properties of the paper web.

5. A method as claimed in claim 1, characterized in that said conversion of the measured values occurs to a numerical of graphic form which indicates variations of the property within an area of the paper web (7) formed by said steps.

6. A method as claimed in claim 5, characterized in that the measured values from each measuring sequence are presented by cartogram.

7. A method as claimed in claim 1, characterized in that a second measuring sequence is performed comprising feeding the paper web (7) at a predetermined, constant, low speed and measuring said property in the measuring section (3) when the paper web (7) passes this at said low speed.

8. A method as claimed in claim 7, characterized in that said low speed is 1 metre/minute and that the second measuring sequence is performed within a length of 10–20 metres of the paper web (7).

9. A method as claimed in claim 7, characterized in that a third measuring sequence is performed which comprises feeding the paper web (7) at a predetermined, constant speed which is higher than said low speed, and measuring said property in the measuring section (3) when the paper web (7) passes this at said higher speed.

10. A method as claimed in claim 9, characterized in that said higher speed is 100 metre/minute.

11. A measuring machine for analyzing at least one property of a paper web (7) manufactured in a defined paper machine from which jumbo rolls (5) are supplied, characterized in that it comprises an unreeling section (1) to support and rotatably journalling a jumbo roll (5) from said paper machine, a reeling section (2) for winding the paper web (7) of the jumbo roll (5) to form a new reel (11) and a measuring section (3) situated between them through which the paper web (7) passes, that the measuring section (3) comprises traversing scanners having a measuring sensor for measuring said property, that the reeling section (2) includes drive means arranged to produce stepwise movement of the paper web (7) through the measuring section (3), and that the measuring section (3) includes a computer unit for storing the measured values recorded by the measuring sensor and processing these values for visual presentation of variations of the property.

12. A measuring machine as claimed in claim 11, characterized in that said drive means are also arranged to produce continuous movement of the paper web (7) at a low speed and at least one additional continuous movement of the paper web (7) at a higher speed than the immediately preceding speed.

* * * * *